United States Patent
Podmore et al.

(10) Patent No.: US 8,402,973 B2
(45) Date of Patent: Mar. 26, 2013

(54) METHOD AND SYSTEM FOR SIZING AN ORAL DEVICE

(75) Inventors: Jonathan L. Podmore, San Carlos, CA (US); Kenneth Mejia, San Francisco, CA (US); Shannon Clark, Palo Alto, CA (US)

(73) Assignee: Apnicure, Inc., Redwood City, CA (US)

( * ) Notice: Subject to any disclaimer, the term of this patent is extended or adjusted under 35 U.S.C. 154(b) by 365 days.

(21) Appl. No.: 12/857,375

(22) Filed: Aug. 16, 2010

(65) Prior Publication Data

US 2012/0037166 A1    Feb. 16, 2012

(51) Int. Cl.
*A61F 5/56* (2006.01)
(52) U.S. Cl. ........................................ 128/848
(58) Field of Classification Search .............. 128/848, 128/859, 860, 861, 862; 602/902; 433/6, 433/33, 37, 72, 73, 75, 513, 514, 26; 434/263, 434/264
See application file for complete search history.

(56) References Cited

U.S. PATENT DOCUMENTS

| | | | | |
|---|---|---|---|---|
| 2,219,559 | A * | 10/1940 | Lentz | 433/55 |
| 3,132,647 | A | 5/1964 | Corniello | |
| 4,169,473 | A | 10/1979 | Samelson | |
| 4,304,227 | A | 12/1981 | Samelson | |
| 4,669,459 | A | 6/1987 | Spiewak et al. | |
| 4,676,240 | A | 6/1987 | Gardy | |
| 4,997,368 | A * | 3/1991 | Mayer et al. | 433/72 |
| 5,385,155 | A * | 1/1995 | Kittelsen et al. | 128/861 |
| 5,465,734 | A | 11/1995 | Alvarez et al. | |
| 5,915,385 | A | 6/1999 | Hakimi | |
| 5,957,133 | A * | 9/1999 | Hart | 128/207.14 |
| 6,494,209 | B2 | 12/2002 | Kulick | |
| 6,736,637 | B2 * | 5/2004 | Bond | 433/20 |
| 6,877,513 | B2 | 4/2005 | Scarberry et al. | |
| 6,955,172 | B2 | 10/2005 | Nelson et al. | |
| 6,976,491 | B2 | 12/2005 | D'Agosto | |
| 7,073,505 | B2 | 7/2006 | Nelson et al. | |
| 7,073,506 | B2 | 7/2006 | Robertson et al. | |
| 7,182,082 | B2 | 2/2007 | Hoffrichter | |
| 7,328,698 | B2 | 2/2008 | Scarberry et al. | |
| 2005/0166928 | A1 | 8/2005 | Jiang | |
| 2005/0166929 | A1 | 8/2005 | Jiang | |
| 2005/0236003 | A1 | 10/2005 | Meader | |
| 2006/0096600 | A1 | 5/2006 | Witt et al. | |
| 2006/0282010 | A1 | 12/2006 | Martin et al. | |
| 2007/0277818 | A1 | 12/2007 | Chen | |
| 2008/0188947 | A1 | 8/2008 | Sanders | |

(Continued)

FOREIGN PATENT DOCUMENTS

WO    WO 2008/083857 A1    7/2008

OTHER PUBLICATIONS

Cartwright et al., "The effects of a non-surgical treatment for obstructive sleep apnea: the tongue retaining device;" JAMA, Aug. 1982; 248(6): 705-709.

(Continued)

*Primary Examiner* — Patricia Bianco
*Assistant Examiner* — Raymond E Harris
(74) *Attorney, Agent, or Firm* — Wilson, Sonsini, Goodrich & Rosati (57) ABSTRACT

Systems for sizing oral applications include both a width measuring template or tool for determining the distance between opposed molars and an arch sizing tool for determining the size and shape of the patient's dental arch. Based on this information, individual appliances can be selected from an inventory of such appliances, where the selected appliance would best fit the patient.

16 Claims, 5 Drawing Sheets

U.S. PATENT DOCUMENTS

| | | |
|---|---|---|
| 2008/0210244 A1 | 9/2008 | Keropian |
| 2008/0216843 A1 | 9/2008 | Jiang |
| 2008/0221697 A1 | 9/2008 | Graser |
| 2009/0120446 A1 | 5/2009 | Vaska et al. |
| 2009/0120447 A1 | 5/2009 | Vaska et al. |
| 2009/0123886 A1* | 5/2009 | Vaska .............................. 433/27 |
| 2011/0195373 A1* | 8/2011 | Waugh ............................ 433/24 |

OTHER PUBLICATIONS

Hoffstein, "Review of oral appliances for treatment of sleep-disordered breathing," Sleep Breath, Mar. 2007;11(1):1-22.

International search report and written opinion dated Nov. 22, 2011 for PCT/US2011/043574.

* cited by examiner

METHOD AND SYSTEM FOR SIZING AN ORAL DEVICE

BACKGROUND OF THE INVENTION

1. Field of the Invention

The present invention relates generally to medical devices and methods. In particular, the present invention relates to a method and a system for sizing an oral device to allow selection of a particular device having a proper fit for an individual patient from an inventory of such devices.

Mouthpieces, mouth guards, and a variety of other oral devices are worn by patients for a variety of purposes. Of particular interest to the present invention, certain oral devices and appliances can be used for treating obstructive sleep apnea (OSA) which is a serious medical condition resulting from temporary airway blockage which occurs as a patient sleeps. A variety of devices have been developed over the years for altering pressure, tongue position, and other characteristics of the oral cavity in order to minimize the occurrence of sleep apnea in patients. One such oral appliance is described in Published US Application 2009/0120446, assigned to the assignee of the present application, the full disclosure of which is incorporated herein by reference.

Many oral appliances are fitted individually to the patient being treated, typically by taking a full dental impression, forming molds from the impression, and preparing devices which closely conform to the patient's dentition and jaws in order to fit the patient with great accuracy. While such highly accurate fittings may in some cases optimize patient comfort, in all cases they will take time, are inconvenient for the patient, and significantly increase the cost of the oral device.

Thus, for a wide class of oral devices, it will be desirable to provide methods and systems for fitting particular devices from inventories of pre-manufactured devices having different sizes and geometry to individual patients. In some cases, such as with athletic and other mouth guards, the fitting can be rather crude. As described, for example, in U.S. Pat. No. 5,385,155, in some instances it is necessary only to provide devices in three sizes (small, medium, and large) where the devices can be selected using a single sizing template 40 which can be compared to a dental impression plate 44 to determine which of the three sizes best fits the patient.

For more complex devices, such as those intended to treat sleep apnea, more accurate sizing means are desirable, and the ability to rapidly choose from a larger inventory of pre-made devices will be of great benefit. The present invention provides such methods and systems which permit treating professionals to rapidly and accurately choose oral devices from larger inventories of such devices.

2. Description of the Background Art

U.S. Pat. No. 5,385,155 has been discussed above. U.S. Patent Publ. No. 2009/0120446 describes oral appliances for treating OSA of the type which can be usefully sized by the methods and systems of the present invention.

BRIEF SUMMARY OF THE INVENTION

The present invention provides methods and systems for selecting appropriately sized oral devices and appliances from inventories of such appliances or devices for dispensing to individual patients. The oral appliances or devices can be relatively simple mouthpieces or mouth guards which are worn over a patient's upper and/or lower teeth in order to protect the teeth during athletic or other endeavors. More usually, the oral devices or appliances will be intended to provide a therapeutic benefit to the patient, typically being intended to treat obstructive sleep apnea (OSA) or other medical conditions. Usually, the inventory of such devices or appliances will differ principally or entirely by size and/or geometry. That is, the devices will be identical except for the dimensions and shape which are intended to fit different patients having different sized oral cavities and dentition. Typically, there will be at least five oral appliances or devices in any inventory, more typically being at least nine such devices, and frequently being ten, twelve, fifteen, or more such devices. When there is a large number of devices, size differences between different devices in the inventory becomes more difficult to discern and methods for sizing having improved accuracy and discrimination are advantageous.

In a first aspect of the present invention, methods are provided for selecting appropriately sized oral appliances from an inventory of such appliances, where individual appliances within the inventory have different sizes and/or geometries selected to conform to the oral cavities and/or dentition of different patients. The methods comprise obtaining an image of a patient's dental arch showing the positions of individual teeth. A width between opposed teeth, usually opposed molars, on the image is then measured, and one arch sizing template is selected from a group of such arch sizing templates based on the measured width. The arch sizing templates are typically clear or translucent sheets of material, such as plastics, having a plurality of arcs with particular shapes, dimensions, and positions printed thereon. Positions are usually relative to a baseline between the opposed molars, the dimensions include the distance from the baseline to the top of the arc as well as the distances between opposed sides of the arc, and the shape is the geometry of the arc. At a minimum, the arc shape should reflect the arch of the front six teeth, between and including the opposed canine teeth, and most often will reflect an entire dental arch. Typically, each arch sizing template will display two, three, four, five, six, or more individual arcs, where the arcs have a common width at their base corresponding to the measured width between opposed molars on the patient's dental image.

After choosing the template having the appropriate molar width at the base of the printed arcs, the template is aligned over the image of the patient's dental arch such that markings on the template at the base of the arch corresponding to the width between the opposed molars (which indicate the width) are aligned over or adjacent to the opposed molars shown on the image of the patient's dental arch.

After the base of the plurality of arcs is aligned with the image, a user can visually or otherwise determine which one of the plurality of arcs on the template align best with the patient's dental arch image. Usually, each of the plurality of arcs will comprise a single arcuate line, and the single line can be aligned above, below, or generally through the individual images of the patient's teeth on the dental image. Usually, the alignment will be a visual "best fit," although it would be possible to use more sophisticated imaging techniques to perform a mathematical "best fit" of the arc to the dental arch.

Once the arc on the template having the best fit to the patient's dental arch is determined, the user can then select the particular dental appliance from the inventory which corresponds to the identified arc on the template. The total number of individual arcs on all of the individual templates will usually correspond to the total number of individual appliances in the inventory. In that way, once an arc has been identified on the template, it will correspond to one and only one appliance in the inventory. Alternatively, it would be possible to provide a total number of arcs on the templates which does not correspond exactly to the number of devices in the inventory. In such cases, it might be possible to provide a table or other means for identifying which template arch or arches correspond to any one device in the inventory. It would also be possible to have two or more devices correspond to a single arc on a template, which might be useful if the devices had other characteristics such as material, color, or differing properties other than size.

In specific aspects of the methods of the present invention, the dental arch image may be obtained by taking a bite wax impression. Alternatively, the image could be obtained using impression paper, crushable foam, alginate or vinyl polysiloxane (PVS) impressions, or even digital scanning techniques, although the latter methods are normally not necessary.

Measuring the width between opposed molars on the image can be performed in various ways. Usually, a separate width sizing template having two, three, four, or more widths marked thereon will be used. The template, which will be a clear plastic sheet as with the arch sizing templates, will be placed over the image of the teeth and right and left hand markers, typically intersecting lines, will be aligned with opposed molars, typically the opposed second molars. Alternatively, a simple ruler or scale could be used to measure the distance between opposed molars, and the measured distance used to select the arch sizing template for further sizing. In still other instances, the width measurements could be made by sequentially aligning the baselines of each of the individual arch sizing templates, although use of a single width sizing template is preferred since the closeness of the fits with each width can be easily compared with each other to choose the best fit.

Usually, the methods will employ a plurality of arch sizing templates with one arch sizing template corresponding to each width marking on the width sizing template (when the width template is employed). Thus, the arch sizing template to be used will correspond to the width measured on the width sizing template. The arch sizing template is then aligned over the image of the dental arch with the arc markings aligned, as described previously.

The methods of the present invention may be used with any oral appliance having structure intended to be held between a patient's teeth, e.g., a bite plate of channels which are received between the teeth on each jaw to hold the device in place. The methods are preferably used with oral appliances intended to treat sleep apnea, typically having structure for drawing a vacuum within the patient's oral cavity.

The present invention further provides systems for selecting appropriately sized oral appliances, such as oral appliances and devices for treating sleep apnea. The systems comprise a bite imaging plate, a molar width measuring tool, and a plurality of arch sizing templates. The bite imaging plate is typically a bite wax plate, but could comprise other media capable of recording the impression of the teeth when applied to the plate. The width measuring tool will typically be a width measuring template, as described above, having a plurality of markings corresponding to particular distances between opposed molars and suitable for placement and alignment over the bite imaging plate. The arch sizing templates will each comprise a plurality of full or partial arcs corresponding to various sized dental arches, with each arch sizing template having markings for a single distance between opposed molars. Thus, after measuring the opposed molars, a specific arch sizing template can be chosen to be aligned over the image of the patient's teeth on the bite imaging plate for determining the size and shape of the dental arch. Once both the molar width and the size and shape of the dental arch are determined, a single dental appliance may be selected from an inventory of such appliances having different sizes and geometry.

As described above in connection with the methods of the present invention, the bite imaging plate is typically a bite wax plate, the width measuring tool is typically a clear template with a plurality of width markings, and the arch sizing templates are typically clear templates each having a plurality of arcs corresponding to the sizes and shapes of different dental arches.

DETAILED DESCRIPTION OF THE INVENTION

Systems according to the present invention will include a tool or component for obtaining an image of a patient's dentition, i.e. all of the teeth in an upper and/or lower jaw, a tool or component for measuring the distance between opposed molars in the upper or lower jaw, usually between the second molars but sometimes between the first molars, and a tool or component for assessing the size and shape of the dental arch to allow a selection of the most appropriate dental appliance from an inventory of such appliances having different sizes.

Figure 1:
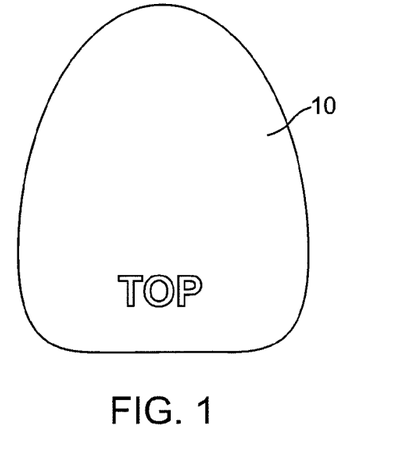
FIG. 1 illustrates a conventional bite wax plate suitable for use in the methods and systems of the present invention.
Figure 2:
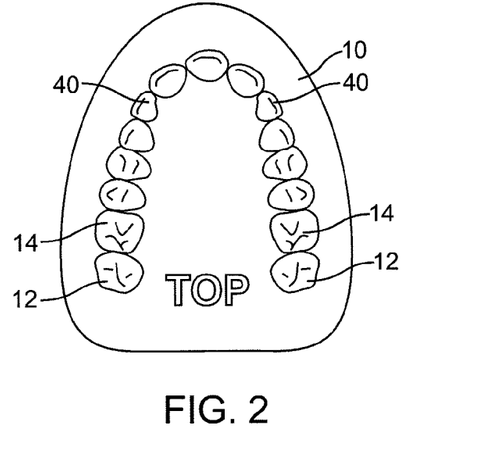
FIG. 2 illustrates the bite wax plate of FIG. 1 shown after a patient has transferred a tooth impression to the plate.

The tool or component for obtaining an image of the dentition will typically be a bite wax impression plate 10, as illustrated in FIG. 1. Such bite wax impression plates are commonly used in the dental and orthodontic fields and are commercially available from suppliers, such as Carmel Dental Wax, Inc., Champlain, N.Y. The bite wax impression plates 10 are used by placing the plate in a patient's mouth, having the patient bite down with an appropriate force so that the individual teeth make indentations into the wax material of the plate. Such impressions leave a very accurate image of the shape of the teeth in the dental arch, as shown in FIG. 2. The teeth shown in FIG. 2 are of a patient with wisdom teeth removed so that second opposed molars 12 lie at the posterior end of the dental arch with the first opposed molars 14 adjacent thereto.

Other tools or components could also be used for obtaining an image of the patient's dental arch. For example, a sheet or film of dyed or pressure-sensitive paper could be used in place of the bite wax impression. The patient would still bite down on the sheet or film to leave the desired image. Similarly, a crushable foam or paper could be used to obtain an impression/image of the teeth of the dental arch. The image could also be obtained optically or by X-rays. Finally, the present invention could use full alginate impressions, although a significant advantage of the present invention is that such full impressions are not necessary.

Figure 3:
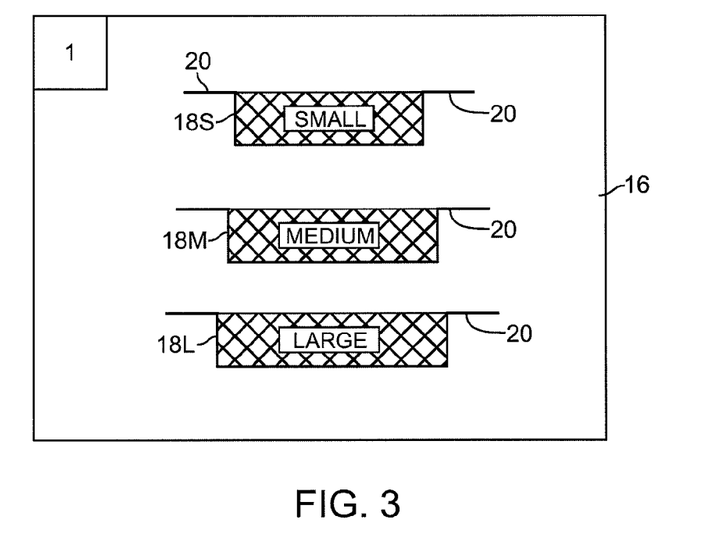
FIG. 3 illustrates a width sizing template useful in the methods and systems of the present invention.
Figure 3A:
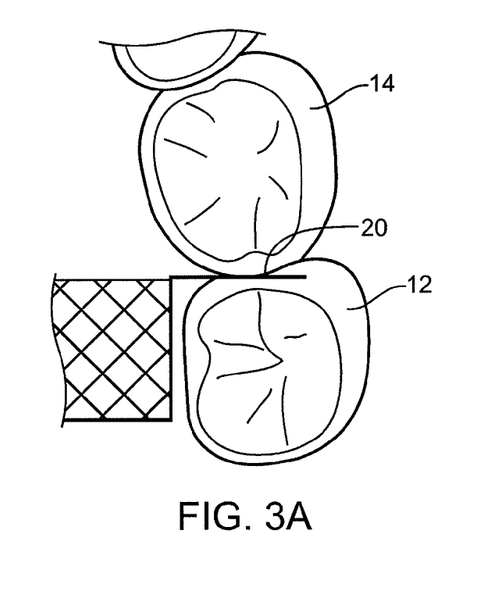
FIG. 3A illustrates placement of a corner the medium molar width template of FIG. 5 over the bite wax plate of FIG. 2.

Once the image has been obtained, the methods of the present invention call for determining the distance or width between opposed molars, either the first or second molars (or possibly the third molars in the case of patients who have not had their wisdom teeth removed). Most conveniently, a template 16, as illustrated in FIG. 3, can be placed over the image as shown in FIG. 2 and the one of a series of bar-like markings 18S, 18M, and 18L aligned to see which of the markings best fits. As shown in FIG. 3A, a corner 20 at each end of the marking 18S/L can be aligned with an extension of the corner position between the first molar 14 and second molar 12 with the end of the marking placed inside of the second molar. The particular marking 18S/18L which best fits between the teeth without extending over either of the molars 12 will determine the width of the dental appliance and allow selection of the arch sizing template to be used to complete the appliance size selection process. While three widths as illustrated in FIG. 3 will usually be sufficient, in some cases it might be desirable to use more.

Figure 4:
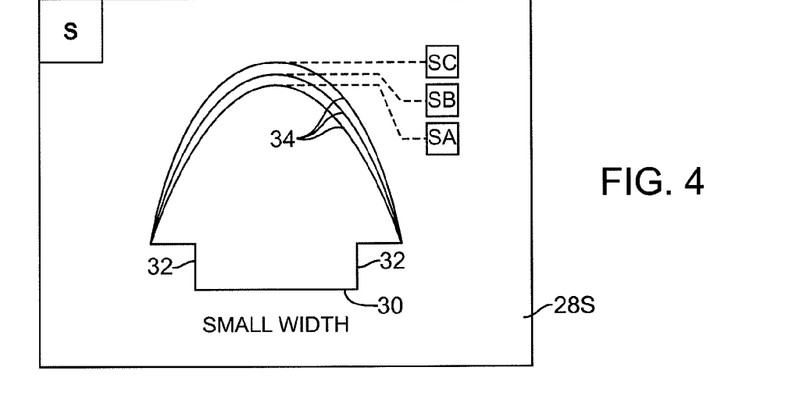
FIGS. 4-6 illustrate arch sizing templates suitable for use in the methods and systems of the present invention, particularly including templates corresponding to a small molar width, a medium molar width, and a large molar width, in FIGS. 4-6, respectively.
Figure 5:
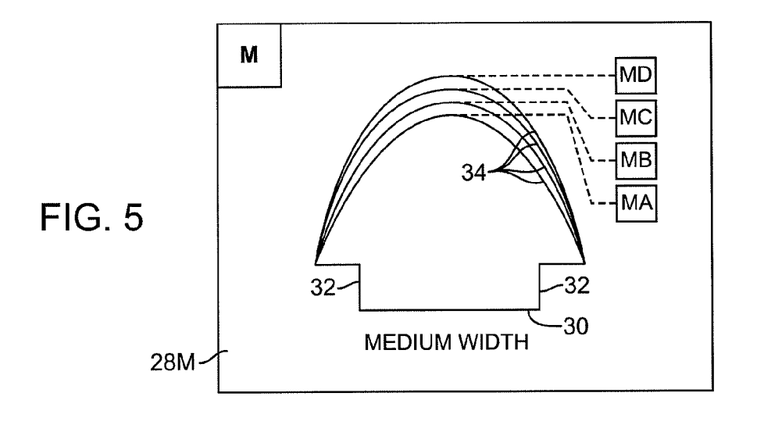
Figure 6:
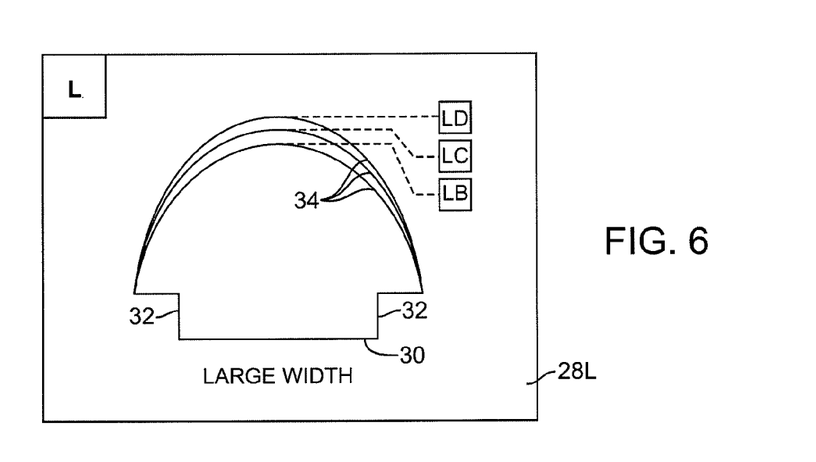

Referring now to FIGS. 4-6, a plurality of arch sizing templates 28S, 28M, and 28L will usually be included in the systems of the present invention. There will be one arch sizing template for each of the different widths which may be selected using the width sizing template 16. Thus, as the width sizing template includes three different widths, there are three arch sizing templates, with one template corresponding to each of the widths. Had there been a different number of widths, there would be a different but corresponding number of arch sizing templates.

Each of the arch sizing templates 28S, 28M, 28L will include a base line 30 having corners 32 which are identically sized to the markings 18 on the width sizing template 16. Extending upwardly from the base 30 are a series of differently sized arc lines SA, SB, SC (FIG. 4), MA. MB. MC, MD (FIG. 5), LB, LC, and LD (FIG. 6) (depending on the number of arcs needed to cover the expected dental arch size range in the patient population). Each arc line 34 on each template 28S, 28M, 28L will be given a unique designation which corresponds to a unique appliance size and/or designation maintained in the inventory of appliances. As illustrated, the designations can be a combination of the appliance width (e.g., S, M, or L) as well as the size of the arch (e.g., A, B, C, D, etc.). Once the arc has been appropriately aligned, as described below in connection with FIG. 9, it will then be an easy matter to select the appropriately sized dental appliance.

Both the width sizing template 16 and the arch sizing templates 28 can be formed from any clear or translucent material, preferably being a clear plastic sheet or film, for example being formed from a polyester polymer. The markings on the template will usually be printed thereon, but could also be embossed, etched, or otherwise formed so that they are clearly visible to the user when the template is placed over the bite wax impression or other image.

Figure 9:
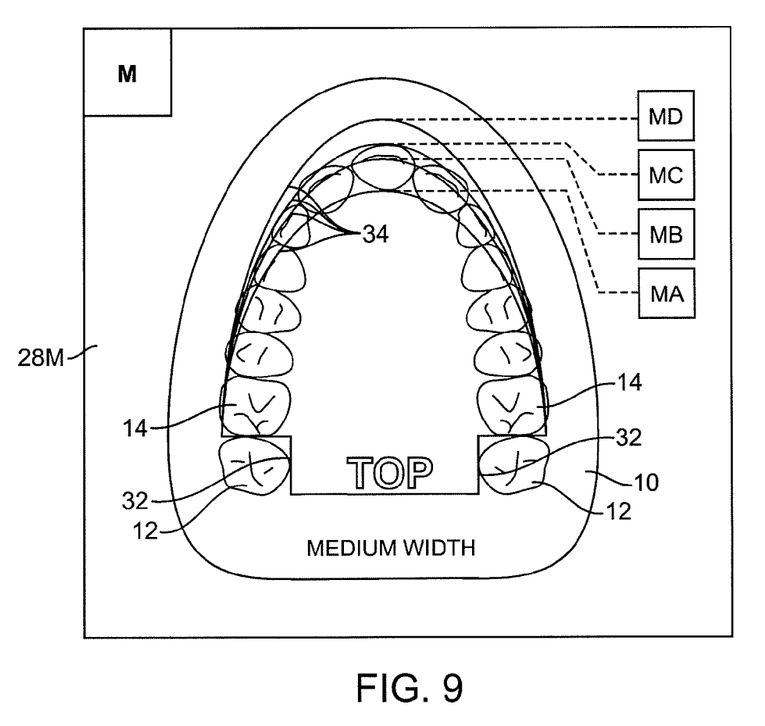
FIG. 9 illustrates the proper alignment of the width markings of the template of FIG. 2 with the second molar of the patient's dentition.

Referring now to FIG. 9, the bite wax impression 10 having the patient's tooth impressions thereon, as illustrated in FIG. 2, has been measured using the width sizing template 16, and a medium width arch sizing template 28M selected to determine the patient arch size. The template 28M is placed over the bite wax impression 10, as illustrated in FIG. 9, with the corners 32 placed over the second molars 12 adjacent to the first molars 14. At this point, the user will determine which of the individual arc lines 34 best aligns with the exterior shape of the patient's dental arch. The user should determine the closest fit, which in this case would be arc line MC. With that determination, the user may select the dental appliance which corresponds to size MC and dispense it to the patient.

Figure 7:
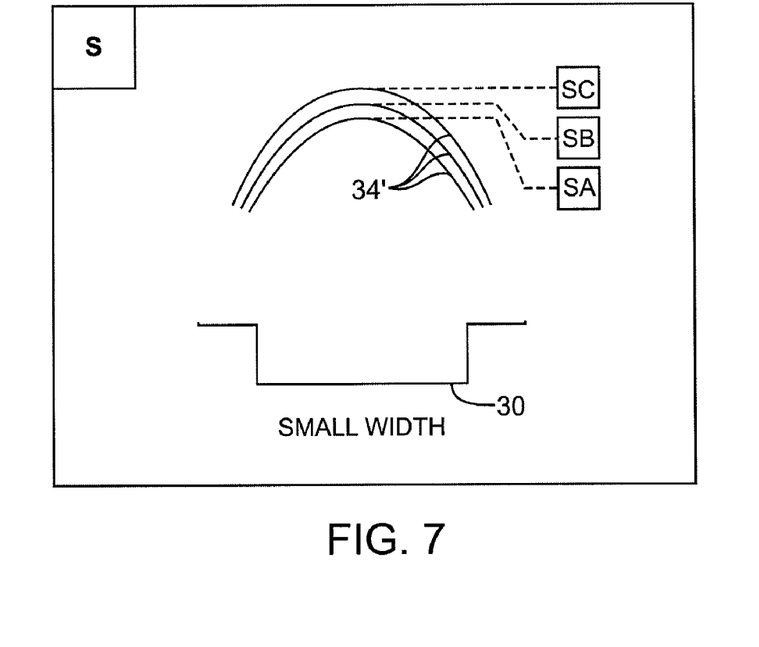
FIG. 7 illustrates an alternative embodiment of the arc template of FIG. 4, shown with a plurality of arc lines corresponding to a partial dental arch.
Figure 8:
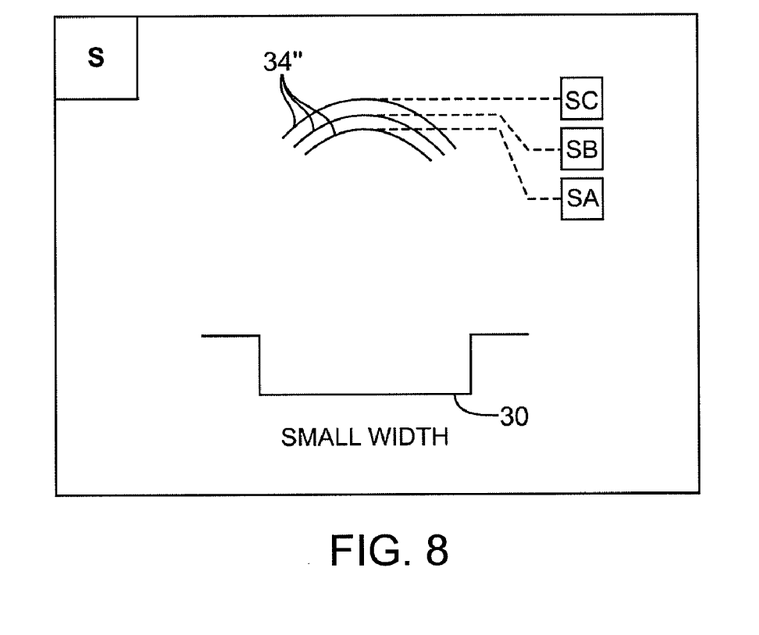
FIG. 8 illustrates another alternative embodiment to the arc template of FIG. 4, shown with even shorter arches corresponding to the front teeth between the canine teeth.

The individual arc lines on the arch sizing templates 28 need not extend fully from one side of the baseline 30 to the other. For example, as shown in FIG. 7, the individual arc lines 34' may extend over only an anterior portion, approximately 50% of the dental arch. Still further alternatively, as shown in FIG. 8, the individual arc lines 34" may extend over only the front or anterior six teeth, i.e., between the canines 40 (as shown in FIG. 2).

Figure 10:
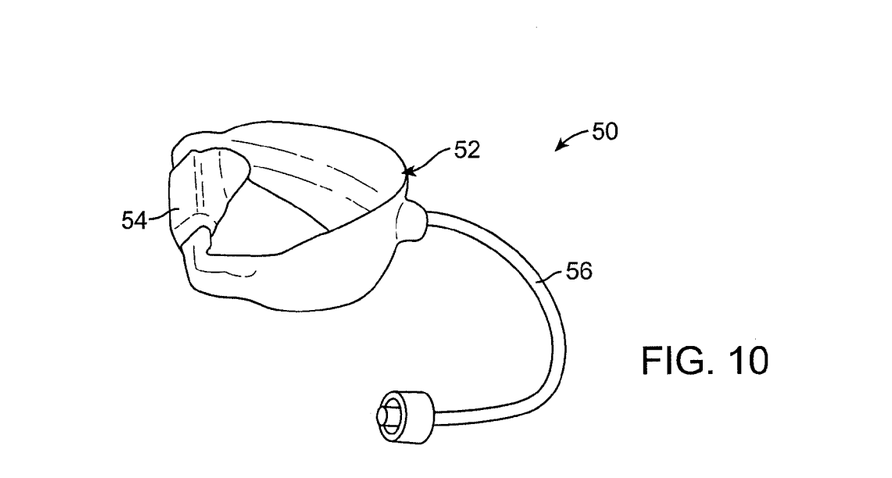
FIG. 10 illustrates one type of oral appliance useful in the sizing methods of the present invention.
Figure 11:
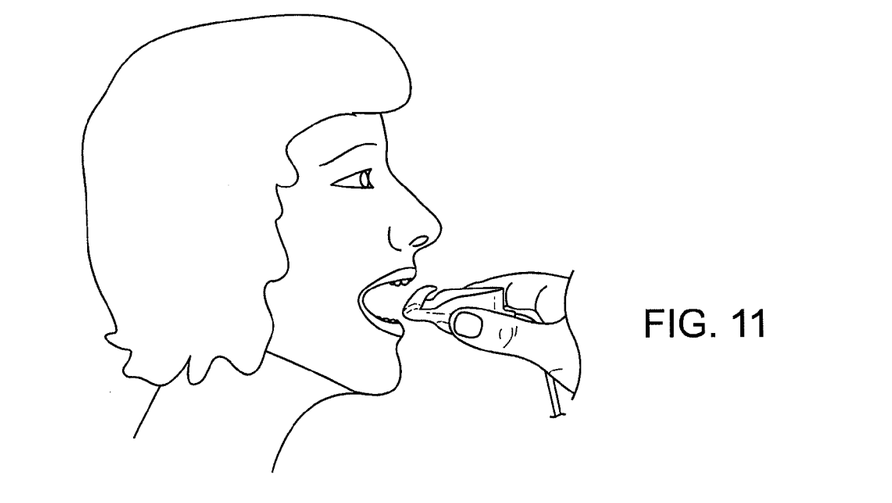
FIG. 11 illustrates placement of the oral appliance of FIG. 11 after proper sizing.
Figure 12:
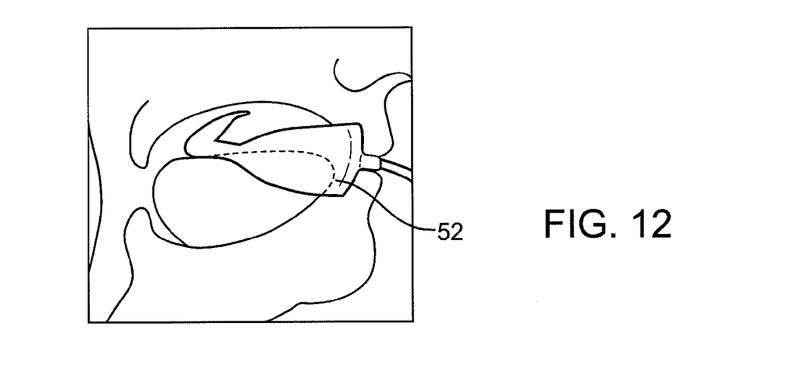
FIG. 12 illustrates placement of the oral appliance in the patient's oral cavity.

Referring now to FIG. 10, an exemplary dental appliance which can be sized using the systems and methods of the present invention comprises an appliance 50 having a base 52 intended for holding between the patient's teeth in order to position a tongue-engaging member 54 against the patient's tongue. Base 52 can be sized using systems and methods described above. Such devices provide for drawing a vacuum in the oral cavity through the tongue-engaging member and include a vacuum line 56 extending from an anterior end thereof. As shown in FIG. 11, once properly sized, the device can be simply placed in the patient's mouth, and the patient can close the teeth over the base 52 to hold the device comfortably in place, as shown in FIG. 12. Such devices are described in more detail in copending application Ser. No. 12/840,076, the full disclosure of which is incorporated herein by reference.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for selecting an appropriately sized oral appliance from an inventory of oral appliances of different sizes, said method comprising:
   obtaining an image of a patient's dental arch showing the positions of individual teeth; determining a width between opposed teeth on the image;
   selecting one arch sizing template from a group of arch templates based on the determined width;
   aligning the arch sizing template over the image of the dental arch so that bottom markings are over or adjacent to the opposed molars;
   determining which one of a plurality of arcs on each of the arch templates aligns best with the patient's dental arch image; and
   selecting an oral appliance having a molar width and arch geometry which best match those of the dental arch on the template which aligned best with the dental arch image.

2. A method as in claim 1, wherein obtaining the dental arch image comprises taking a bite wax impression.

3. A method as in claim 1, wherein determining the width comprises aligning opposed molars on the image with one of a plurality of width markings on a width sizing template.

4. A method as in claim 3, wherein there are a plurality of arch sizing templates with one arc template corresponding to each width marking on the width template, wherein selecting the arc template comprises selecting the one arch template which corresponds to the aligned width marking.

5. A method as in claim 1, wherein determining the width comprises aligning opposed molars on the image with a width marking on each of the group of arch templates.

6. A method as in claim 5, wherein the arcs on the arch sizing template correspond to the front teeth between the canine teeth.

7. A method as in claim 5, wherein the arcs on the arch sizing template correspond to the full dentition between the opposed molars.

8. A method as in claim 1, wherein the oral appliance comprises structure for drawing a vacuum to treat sleep apnea.

9. A system for selecting an appropriately sized oral appliance, said system comprising:
- a bite imaging plate to obtain an image of a patient's dental arch;
- a measuring tool to determine a distance between opposed teeth on an image of the patient's dental arch on the bite plate; and
- a plurality of arch sizing templates, wherein each of said templates corresponds to a single measured distance between opposed teeth and includes a multiplicity of arcs corresponding to dental arch profiles;

wherein a single template can be selected based on a measured distance between opposed molars and the template aligned over the bite plate image to determine which of the multiplicity of arch profiles on that template best aligns with the image.

10. A system as in claim 9, wherein the bite plate is a wax plate.

11. A system as in claim 9, wherein the measuring tool comprises a clear width template having at least two width markings thereon.

12. A system as in claim 11, wherein there is one arch sizing template of the plurality of arch sizing templates for each width marking on the width template.

13. A system as in claim 12, wherein each arch sizing template of the plurality of arch sizing templates is a clear template having a width marking similar to a corresponding width marking on the width template and wherein the multiplicity of arcs extend between the width markings.

14. A system as in claim 12, wherein the multiplicity of arcs correspond to the front teeth between the canines.

15. A system as in claim 9, further comprising an inventory of oral appliances including one sized to correspond to each individual combination of measured distance between opposed teeth and each arch profile.

16. A system as in claim 9, wherein the opposed teeth are opposed molars.

* * * * *